(12) United States Patent
Gatti et al.

(10) Patent No.: US 7,169,131 B2
(45) Date of Patent: Jan. 30, 2007

(54) DEVICE FOR ADMINISTERING AN INJECTABLE PRODUCT

(75) Inventors: Stephan Gatti, Hasle-Ruegsau (CH); Thomas Gurtner, Koppigen (CH)

(73) Assignee: TecPharma Licensing AG, Burgdorf (CH)

( * ) Notice: Subject to any disclaimer, the term of this patent is extended or adjusted under 35 U.S.C. 154(b) by 580 days.

(21) Appl. No.: 10/396,537

(22) Filed: Mar. 25, 2003

(65) Prior Publication Data
US 2003/0187405 A1   Oct. 2, 2003

Related U.S. Application Data

(63) Continuation of application No. PCT/CH01/00469, filed on Jul. 31, 2001.

(30) Foreign Application Priority Data
Sep. 26, 2000   (DE) ............................... 100 47 637

(51) Int. Cl.
*A61M 5/00* (2006.01)
(52) U.S. Cl. ........................ 604/207; 604/187
(58) Field of Classification Search ................ 604/181, 604/187, 207–210, 212, 218, 221, 224, 230
See application file for complete search history.

(56) References Cited
U.S. PATENT DOCUMENTS 5,354,286 A * 10/1994 Mesa et al. ................. 604/230
6,193,698 B1 * 2/2001 Kirchhofer et al. .......... 604/211
6,699,224 B2 * 3/2004 Kirchhofer et al. .......... 604/208
2001/0051792 A1 * 12/2001 Kirchhofer et al. .......... 604/209
2002/0016571 A1 * 2/2002 Kirchhofer et al. .......... 604/218

FOREIGN PATENT DOCUMENTS

DE        19900792        6/2000
EP         0962229       12/1999

* cited by examiner

Primary Examiner—LoAn H. Thanh
(74) Attorney, Agent, or Firm—Dorsey & Whitney LLP

(57) ABSTRACT

A device for administering an injectable product in doses including a casing, a reservoir for the product, a piston which displaces product towards a reservoir outlet and out of the reservoir when it slides in an advancing direction, a drive member which may be slid along a sliding axis, thereby pushing the piston in the advancing direction, and a dosing member which is mounted in the casing and may be slid, preferably rotatably, about the sliding axis of the drive member for setting a product dose, wherein a bearing surface between the dosing member and the casing is lubricated and at least one lubricating agent reservoir is provided on the bearing surface.

10 Claims, 2 Drawing Sheets

DEVICE FOR ADMINISTERING AN INJECTABLE PRODUCT

CROSS-REFERENCE TO RELATED APPLICATIONS

This application is a continuation of International Patent Application PCT/CH01/00469, filed on Jul. 31, 2001, which claims priority to German Patent Application No. 100 47 637.6, filed on Sep. 26, 2000, the contents of which are incorporated herein by reference.

SUMMARY

The invention relates to a devices for administering an injectable product. An injection device or apparatus in accordance with the present invention also relates to what is known from WO 97/36625 and DE 199 00 792 C1. The injection apparatus of the present invention comprises a casing, a product reservoir including a piston accommodated in it such that it can slide and displace product from the reservoir when it slides in an advancing direction, a drive means, and a dosing means.

The drive means comprises a drive member which can slide in the advancing direction and a driven member which is prevented from sliding counter to the advancing direction, but which is slaved by the drive member when the drive member slides in the advancing direction thereby pushing the piston in the advancing direction, such that product is displaced from the reservoir. The product is deliverable in selected dosages set or chosen by means of the dosing means.

The dosing means comprises the drive member and a dosing member for setting the distal end position of the drive member. The dosing member is mounted in the casing, rotatable about the axis along which the drive member moves or slides axially. In one embodiment, it preferably comprises a dosing stopper revolving spirally about the sliding axis, preferably with a continuous course and a constant gradient relative to the sliding axis of the drive member, said drive member abutting said dosing stopper when it slides into the distal position, i.e., the rotational angular position of the dosing member determines the distal position of the drive member.

The deliverable product dosage is selected by rotating the dosing member, in one embodiment preferably in discrete steps. To this end, the dosing member locks in rotational angular locking positions formed at regular intervals between the casing and the dosing member. Rotating the dosing member between two adjacent locking positions corresponds to the smallest settable product dosage.

SUMMARY

An object of the present invention is to provide a device for administering an injectable product, in particular of the aforementioned type, which enables a user to easily dose a product, wherein the dosing precision and accuracy of previously known devices is at least maintained. In particular, easy rotation of the dosing member is ensured.

This object is addressed by the injection device of the present invention, which comprises a bearing surface between the dosing member and the casing, wherein the bearing surface is lubricated. In one embodiments, at least one lubricating agent reservoir is provided on or near the bearing surface. The present invention also encompasses a method of providing a lubricated bearing surface.

In one embodiment, the present invention comprises a device for administering an injectable product in doses, said device comprising a casing, a drive member moveable along a sliding axis, a dosing member operably moveable about the sliding axis of the drive member for setting a product dose, and a bearing surface between said dosing member and the casing, the bearing surface being lubricated. At least one lubricating agent reservoir is operably adjacent to the bearing surface. The dosing member is operably coupled to the casing by an annular bulge, such that it can slide axially, and the bearing surface is formed by at least one surface of the annular bulge. In one embodiment, the annular bulge is provided on the dosing member and is axially held in an annular groove in the casing. In one embodiment, the at least one lubricating agent reservoir is formed by a flattened portion of the annular bulge.

By lubricating the bearing surface, friction between the dosing member and the casing is reduced. The movement, preferably rotation, of the dosing member which has to be performed for dosing is made easier for the user. By providing at least one lubricating agent reservoir, sufficient lubricating agent can be provided to avoid the need for a secondary supply of lubricating agent during the entire usable life of the device. Thus, lifetime lubrication is ensured. This simplifies using the device.

In one embodiment, the lubricating agent reservoir is preferably provided in the immediate vicinity of the bearing surface. In one embodiment, it is preferably formed by a hollow space or relieved area in the dosing member or in the casing.

In one embodiment, the dosing member is preferably mounted in the casing, rotatable about the sliding axis of the drive member and secured against sliding axially. Particularly preferably, there is no longitudinal play between the dosing member and the casing. This ensures exact dosing in the device. A high surface pressure therefore prevails in the bearing surface between the dosing member and the casing. This high surface pressure results in a high torque which, however, is effectively reduced by lubricating.

In one preferred embodiment, the dosing member is mounted on the casing, secured against sliding axially via an annular bulge. The annular bulge is preferably arranged on the surface area of the dosing member which is in contact with the casing, and protrudes into a recess in the surface area of the casing. In this way, an undercut is produced between the dosing member and the casing. In principle, however, the annular bulge could also be provided on the casing. A surface of the annular bulge at an angle to the sliding axis forms a bearing surface for the axial mount of the dosing member. Preferably, this surface is lubricated and at least one lubricating agent reservoir is provided on it. The lubricating agent reservoir is arranged such that the lubricating agent situated in it comes into contact with the bearing surface when the dosing member is rotated.

In some embodiments, a second bearing surface for the axial mount of the dosing member is also lubricated and at least one lubricating agent reservoir is provided on it. This second bearing surface can be formed by another surface of the annular bulge or by another surface of the dosing member or the casing.

In one embodiment, the annular bulge is preferably provided on the dosing member and axially held in a recess in the casing. The dosing member is arranged within the casing such that the annular bulge radially projects from the outer surface area of the dosing member into an annular groove provided on the inner surface area of the casing.

In some embodiments, the lubricating agent reservoir is preferably formed by a flattening of the annular bulge. In one preferred embodiment, the annular bulge is interrupted at the point at which the lubricating agent reservoir is provided. The interruption in the annular bulge creates a hollow space between the dosing member and the annular groove in the casing. Any suitable lubricating agent can be stored in this hollow space. One advantage of the lubricating agent reservoir is that, while the lubricating agent is pressed away from the bearing surface as the dosing member is assembled in the casing, the bearing surface is adjacent to, travels near or contacts a lubricating agent reservoir during rotation such that constant re-lubricating is ensured. The lubricating agent also remains at the desired point after assembly.

In some preferred embodiments, a number of lubricating agent reservoirs may be arranged or distributed, including uniformly distributed, over the circumference of the dosing member or the casing. This ensures that the bearing surface is better lubricated. In one preferred embodiment, four lubricating agent reservoirs are provided.

In one embodiment, grease is used as the lubricating agent, particularly preferably Molykote grease. The lubricating agent reservoirs are thus provided as pockets of grease.

BRIEF DESCRIPTION OF THE DRAWINGS

An exemplary preferred embodiment of the present invention is explained below with reference to the accompanying figures.

DETAILED DESCRIPTION

Figure 1:
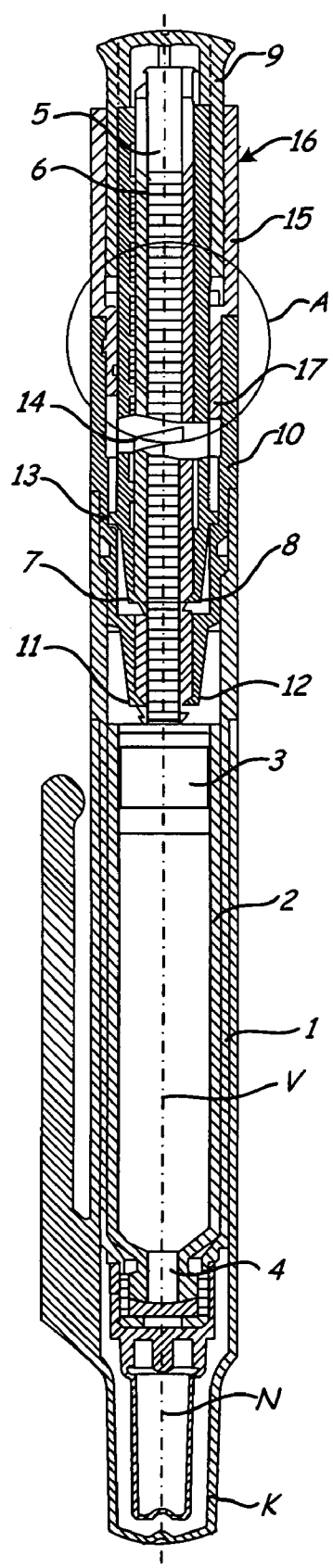
FIG. 1 depicts an injection device comprising a dosing means, in longitudinal section.
Figure 2:
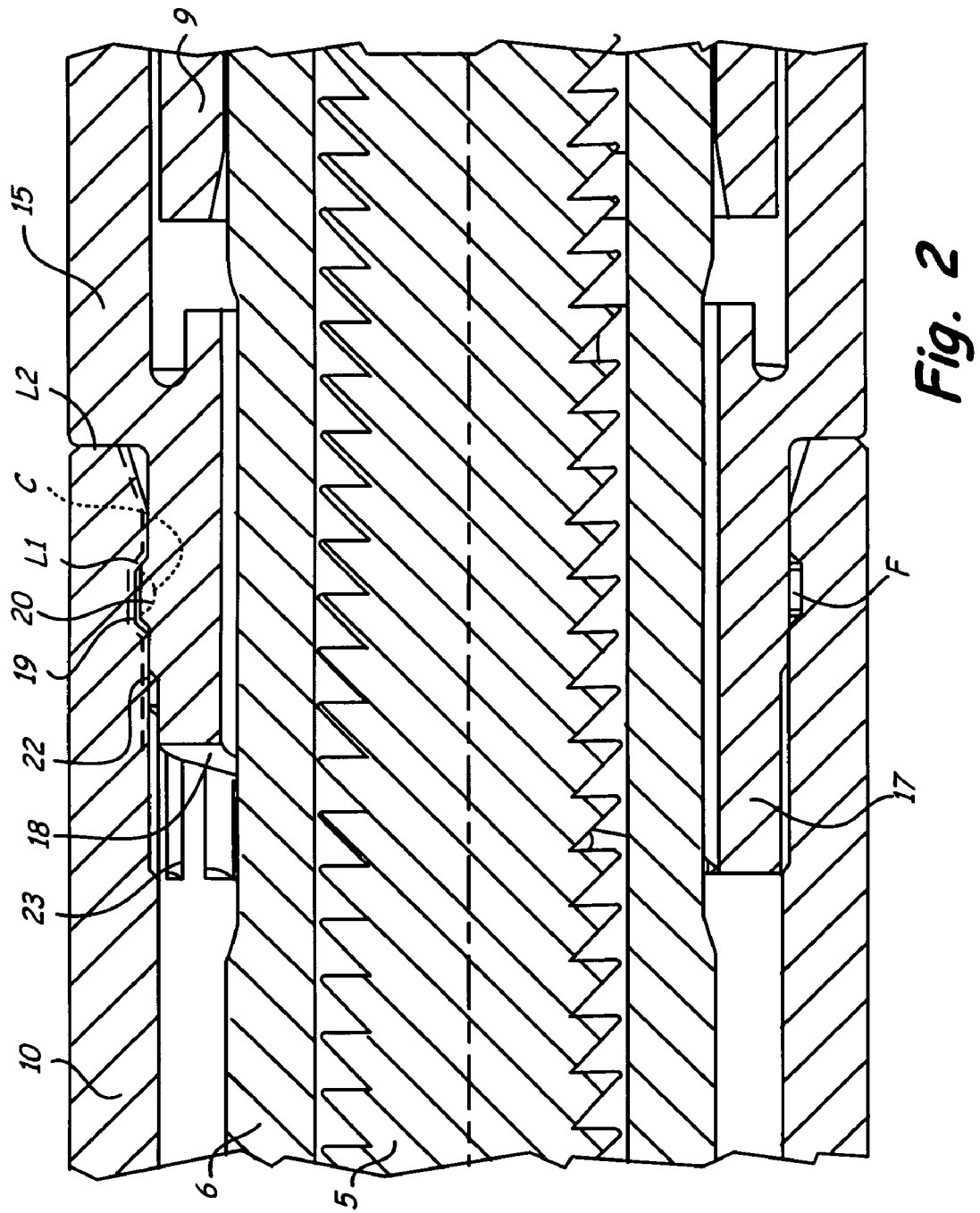
FIG. 2 depicts a dosing member comprising a lubricating agent reservoir in accordance with the present invention, corresponding to Detail area A of FIG. 1.

FIG. 1 shows an injection apparatus, in the exemplary embodiment an injection pen, in longitudinal section. FIG. 2 shows Detail area A of FIG. 1.

The injection apparatus comprises a casing including a front casing sleeve 1 and a rear casing sleeve 10 fixedly connected to the front casing sleeve 1. The front casing sleeve serves as a receptacle for an ampoule 2. A liquid product in the form of an active agent solution, for example insulin, is contained in the ampoule 2. Furthermore, a piston 3 is accommodated in the ampoule 2. By sliding the piston 3 in the advancing direction, i.e., towards an ampoule outlet 4, the product is displaced from the ampoule 2 through its outlet 4 and delivered through an injection needle N, which can be any size, including 31 G or a higher or lower Gauge number. The front casing sleeve 1 is protected by a cap K, as is the needle N.

The piston 3 is slid in the advancing direction by a drive means accommodated in the rear casing sleeve 10. The drive means comprises a toothed rack 5 as a driven member which acts directly on the piston 3, and a drive member 6. The drive member 6 mounted in the rear casing sleeve 10 such that it can be linearly slid along the sliding axis V in and counter to the advancing direction of the piston 3. A cover 9, which is connected to the drive member 6 such that it can slide and freely rotate, protrudes backwards out of the casing.

A dosing member 15 provided as a sleeve body is connected to the rear casing sleeve 10, secured against sliding but rotatable about a common longitudinal axis which corresponds to the sliding axis V. The dosing member 15 protrudes into the rear casing sleeve 10 via a front sleeve portion 17. Its rear sleeve portion protrudes out of the rear casing sleeve 10. The rear sleeve portion of the dosing member 15 is provided with a contour 16 so that it can be rotated with a secure manual grip.

As is seen by referring to FIG. 2, an annular bulge 20 provided on the front sleeve portion 17 of the dosing member 15 and latched into a circumferential recess 19 on the inner surface of the rear casing sleeve 10 serves to fix the dosing member 15 such that it is secured against sliding. A bearing surface L1 of the annular bulge 20 comes into contact with an undercut surface of the recess 19 of the rear casing sleeve 10. Any suitable complementary fixing structure may be used to fix the dosing member, and any suitable shape or arrangement may be used to provide for the bulge 20 and recess 19. A second bearing surface L2 is formed between the rear end of the rear casing sleeve 10 and a circumferential, radially protruding projection of the dosing member 15. The dosing member 15 is mounted in the casing, secured against axially sliding, between the bearing surfaces L1 and L2.

In front of the contour 16 (see FIG. 1), the dosing member 15 may have a suitable, clearly visible dosage scale (not shown, but well known in the art) around its outer surface area, the scale being adjusted to established rotational angular positions in which the dosing member 15 locks against the rear casing sleeve 10. The locking mechanism between the dosing member 15 and the rear casing sleeve 10 is formed by elevations on the outer surface of the front sleeve portion 17 of the dosing member 15, and cavities 23 are formed in the inner surface of the rear casing sleeve 10. The cavities 23 are circumferentially arranged on a level, alongside each other, at equal angular intervals on the inner surface of the rear casing sleeve 10. In the fixed rotational angular locking positions of the dosing member 15, the number of elevations are accommodated precisely in the respectively opposing cavities in the inner surface of the rear casing sleeve 10.

When the injection apparatus is completely assembled, as shown in FIG. 1, the drive member 6 protrudes through the dosing member 15. The dosing member 15 concentrically surrounds a distal portion of the drive member 6 and also of the driven member 5. The cover 9 protrudes via a sleeve portion into an annular gap formed between the drive member 6 and the dosing member 15. As is known to those skilled in the art, the cover 9 may also bear a marking in its surface region protruding out of the dosing member 15, which in cooperation with the marking on the dosing member 15 enables the total amount of product administered from the ampoule 2 to be determined exactly, even after a number of complete rotations of the dosing member 15.

The maximum dosage path length which the drive member 6 and the toothed rack 5 can travel in the advancing direction, and therefore also the maximum product dosage which may be delivered in an injection, also if the size of the needle is 31 G or a higher Gauge number, is set by rotating the dosing member 15.

The smaller the axial play of the dosing member 15 in the rear casing sleeve 10, the more exact the dosage of the device. The dosing member 15 is preferably accommodated in the rear casing sleeve 10 with no play. This, however, increases the surface pressure on or between the bearing surfaces L1, L2, such that a higher torque would be required from the user to set the dosage. By lubricating at least the one of the bearing surfaces L1, L2 this torque can be reduced. Since at a high surface pressure the lubricating agent would be displaced from the bearing surfaces L1, L2 during assembly or operation, lubricating agent reservoirs F are provided to help establish and maintain a contact between the bearing surfaces L1, L2 and the lubricating agent.

A lubricating agent reservoir F is formed by an interruption in sections of the annular bulge 20. This results, in sections, in an intermediate space between the dosing member 15 and the casing sleeve 10. This intermediate space can be filled with lubricating agent, such as grease, and serves to provide lifetime lubrication for the bearing surface L1. In some preferred embodiments, a number of lubricating agent reservoirs F are arranged in uniform distribution over the circumference. The more lubricating agent reservoirs F are provided, the more often the bearing surface L1 brushes over a lubricating agent reservoir F when rotated. The section of FIG. 2 runs through the annular bulge 20 in the upper region of the drawing and through a lubricating agent reservoir F in the lower region of the drawing.

FIG. 2 depicts a further development of a lubricating agent reservoir F in which its volume is increased by additionally providing a suitably shaped cavity C (shown in phantom; any suitable shape may be used) in the dosing member 15 in the region of the interruption in the annular bulge 20. It should be appreciated that the annular bulge 20 could be arranged on the rear casing sleeve 10, with the lubricating agent reservoir F provided therein as well. It should also be appreciated that lubricating agent reservoirs can also be provided in the bearing surface L2, analogously to the lubricating agent reservoirs F in the annular bulge 20. Preferably, in some embodiments, the reservoirs F are formed by recesses in the radial facing surface of the dosing member 15 or of the rear end surface of the rear casing sleeve 10. In some embodiments, lubricating agent reservoirs F are only provided in the bearing surface L1. They can, however, also be provided in the bearing surface L2. In some preferred embodiments, lubricating agent reservoirs F may be situated in both bearing surfaces L1 and L2.

Before the dosing member 15 is assembled, the region 22 of the rear casing sleeve 10 indicated in FIG. 2 by a broken line is provided with lubricating agent. When, to assemble it, the dosing member 15 is pushed into the rear casing sleeve 10, the lubricating agent remains behind in the region of the lubricating agent reservoirs F and ensures that the bearing surfaces L are lubricated when the dosing member 15 is rotated.

Dosing is performed in a proximal end position of the drive member 6, foremost with respect to the advancing direction, in which position a stopper cam or collar 13 protruding radially from the outer surface area of the drive member 6 abuts a stopper formed by the rear casing sleeve 10. In this proximal end position of the drive member 6, the dosing member 15 is rotated about the sliding axis V relative to the rear casing sleeve 10 until it has reached the desired dosing or rotational angular locking position. In this dosing position, a slight dosing interval remains between another collar or cam (which may be known as the dosing cam) which likewise projects from the outer surface area of the drive member 6 and forms the dosing stopper and the proximal facing side 18 of the dosing member 15 opposite said dosing cam 14. The drive member 6 can be retracted counter to the advancing direction, relative to the rear casing sleeve 10 and therefore also relative to the piston 3, by the dosing interval. It is retracted manually by pulling on the cover 9. The dosing interval is equal to the dosage path length when the product is subsequently administered.

When the drive member 6 is slid back or retracted, the toothed rack 5 remains in its sliding position relative to the casing, assumed during the dosing process. The toothed rack 5 is secured against sliding counter to the advancing direction by blocking means 11 and 12 provided on the rear casing sleeve 10. In one embodiment, the blocking means 11 and 12 are locking cams provided on each of the front ends of an elastically flexible tongue, and protrude from their tongue radially inwards towards the toothed rack 5. The blocking means 11 and 12 each cooperate with a row of teeth of the toothed rack 5 facing them, such that they allow the toothed rack 5 to slide in the advancing direction and prevent it from sliding counter to the advancing direction using a positive-lock blocking mesh or connection. Once the drive member 6 has been retracted, it can be slid in the advancing direction by the dosage path length, thereby slaving the toothed rack 5 and the piston 3, such that a dosed amount of the injectable product is displaced from the reservoir 2.

In the foregoing description, embodiments of the invention, including preferred embodiments, have been presented for the purpose of illustration and description. It is not intended to be exhaustive or to limit the invention to the precise forms disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for administering an injectable product in doses, said device comprising:
   a) a casing, comprising a reservoir for said product;
   b) a piston, which displaces product towards a reservoir outlet and out of said reservoir when it slides in an advancing direction;
   c) a drive member, which may be slid along a sliding axis, thereby pushing said piston in said advancing direction;
   d) a dosing member, which is mounted in said casing and may be slid about said sliding axis of the drive member, for setting a product dosage which may be delivered when the product is administered;
   e) a lubricated bearing surface between said dosing member and the casing; and
   f) at least one lubricating agent reservoir provided on said one bearing surface.

2. The device as set forth in the claim 1, wherein said dosing member may be rotated about said sliding axis of the drive member.

3. The device as set forth in claim 1, wherein the dosing member is mounted on the casing via an annular bulge, such that it can slide axially, and the bearing surface is formed by at least one surface of said annular bulge.

4. The device as set forth in the claim 3, wherein the annular bulge is provided on the dosing member and is axially held in an annular groove in the casing.

5. The device as set forth in claim 3, wherein said at least one lubricating agent reservoir is formed by a flattening of the annular bulge.

6. A device for administering an injectable product in doses, said device comprising:
   a casing comprising a reservoir for the product;

a piston slidably coupled to the reservoir for displacing product out of the reservoir when the piston slides in an advancing direction;

a drive member moveable along a sliding axis to push said piston in said advancing direction;

a dosing member operably coupled to said casing and moveable about said sliding axis of the drive member for setting a product dose;

a bearing surface between said dosing member and the casing, said bearing surface being; and at least one lubricating agent reservoir operably adjacent to said bearing surface.

7. A device for administering an injectable product in doses, said device comprising:

a casing;

a drive member moveable along a sliding axis;

a dosing member operably moveable about said sliding axis of the drive member for setting a product dose;

a bearing surface between said dosing member and the casing, said bearing surface being lubricated; and at least one lubricating agent reservoir operably adjacent to said bearing surface.

8. The device as set forth in claim 7, wherein the dosing member is operably coupled to the casing by an annular bulge, such that it can slide axially, and the bearing surface is formed by at least one surface of said annular bulge.

9. The device as set forth in claim 8, wherein the annular bulge is provided on the dosing member and is axially held in an annular groove in the casing.

10. The device as set forth in claim 9, wherein said at least one lubricating agent reservoir is formed by a flattened portion of the annular bulge.

* * * * *

UNITED STATES PATENT AND TRADEMARK OFFICE
CERTIFICATE OF CORRECTION

PATENT NO. : 7,169,131 B2
APPLICATION NO. : 10/396537
DATED : January 30, 2007
INVENTOR(S) : Stephen Gatti and Thomas Guttner It is certified that error appears in the above-identified patent and that said Letters Patent is hereby corrected as shown below:

Claims:

| Col. | Line | PTO | Should Read |
|---|---|---|---|
| 7 | 10 | " being; and " | -- being lubricated; and -- |

Signed and Sealed this

Fifteenth Day of May, 2007

JON W. DUDAS
*Director of the United States Patent and Trademark Office*